(12) United States Patent
Jessup

(10) Patent No.: US 10,849,923 B1
(45) Date of Patent: Dec. 1, 2020

(54) HYALURONIC ACID FORMULATION

(71) Applicant: Donald Wayne Jessup, Campton, KY (US)

(72) Inventor: Donald Wayne Jessup, Campton, KY (US)

( * ) Notice: Subject to any disclaimer, the term of this patent is extended or adjusted under 35 U.S.C. 154(b) by 0 days.

(21) Appl. No.: 15/651,892

(22) Filed: Jul. 17, 2017

Related U.S. Application Data

(63) Continuation-in-part of application No. 15/031,652, filed on Apr. 22, 2016, now abandoned.

(60) Provisional application No. 61/894,818, filed on Oct. 23, 2013, provisional application No. 62/365,546, filed on Jul. 22, 2016.

(51) Int. Cl.
| | | |
|---|---|---|
| *A61K 31/728* | (2006.01) | |
| *A61K 9/00* | (2006.01) | |
| *A61K 9/08* | (2006.01) | |
| *A61K 47/40* | (2006.01) | |
| *A61K 47/12* | (2006.01) | |
| *A23L 33/10* | (2016.01) | |

(52) U.S. Cl.
CPC ............ *A61K 31/728* (2013.01); *A23L 33/10* (2016.08); *A61K 9/0053* (2013.01); *A61K 9/08* (2013.01); *A61K 47/12* (2013.01); *A61K 47/40* (2013.01); *A23V 2002/00* (2013.01)

(58) Field of Classification Search
CPC ..................................................... A61K 31/728
USPC ....................................... 536/1.11; 435/173.2
See application file for complete search history.

(56) References Cited

U.S. PATENT DOCUMENTS

| | | | |
|---|---|---|---|
| 2005/0129829 A1* | 6/2005 | Hosoya .................. | A23F 3/163 426/597 |
| 2012/0258087 A1* | 10/2012 | Jedlinski .................. | A23L 2/39 424/94.1 |
| 2015/0051168 A1* | 2/2015 | Kim ...................... | A61K 31/728 514/54 |

FOREIGN PATENT DOCUMENTS

EP 2155161 B1 * 12/2016 ............. A61K 47/02

* cited by examiner

*Primary Examiner* — Susan M Hanley
*Assistant Examiner* — Paul C Martin

(57) ABSTRACT

The present invention provides solid formulations of hyaluronic acid (HA) that are resistant to degradation into low molecular weight species of HA and yet can be readily dissolved in water. The compositions comprise sodium hyaluronate, cyclo-dextrin, sodium benzoate, and potassium sorbate, wherein said composition is in powder form.

3 Claims, No Drawings

HYALURONIC ACID FORMULATION

RELATED APPLICATIONS

This application is a continuation-in-part of U.S. patent application Ser. No. 15/031,652, filed Oct. 23, 2014, now abandoned, which application claimed priority to U.S. Provisional Patent Application No. 61/894,818, filed Oct. 23, 2013. This application claims priority to U.S. Provisional Patent Application No. 62/365,546, filed Jul. 22, 2016, the entirety of which is incorporated herein by reference.

FIELD OF THE INVENTION

The present invention relates to formulations of hyaluronic acid, in particular, dry powder formulations of hyaluronic acid that are readily dissolved in water and useful as a dietary supplement for improving joint and ligament movement.

BACKGROUND OF THE INVENTION

Hyaluronic acid, also referred to as hyaluronan or hyaluronate or HA, is an anionic, nonsulfated glycosaminoglycan polymer of disaccharides, composed of D-glucuronic acid and D-N-acetylglucosamine, linked via alternating .beta.-1,4 and .beta.-1,3 glycosidic bonds. HA can be 25,000 disaccharide repeats in length and range in weight from 5 to 20,000 kDa in vivo. The average 70 kg (154 lbs) person has roughly 15 grams of hyaluronan in the body, one-third of which is turned over (degraded and synthesized) every day.

In vivo, HA is synthesized by a class of integral membrane proteins called hyaluronan synthases, of which vertebrates have three types: HAS1, HAS2, and HAS3. These enzymes lengthen hyaluronan by repeatedly adding glucuronic acid and N-acetylglucosamine to the nascent polysaccharide as it is extruded via ABC-transporter through the cell membrane into the extracellular space.

HA is an important component of articular cartilage, where it is present as a coat around each chondrocyte and is a major component of the synovial fluid providing essential lubrication in joints. When HA binds to the proteoglycan aggrecan in the presence of link protein, large, highly negatively charged aggregates form. These aggregates imbibe water and are responsible for the resilience of cartilage to compressive loads. The average molecular weight HA in human synovial fluid is 3,000 to 4,000 kDa, though this decreases with age.

HA has been used for human and veterinary purposes. For example, HA is used in treatment of articular disorders in horses, in particular those in competition or heavy work. It is indicated for carpal and fetlock joint dysfunctions. In the 1990s, HA became available as a treatment for knee osteoarthritis. For people with severe knee arthritis, injecting HA into the joint provides substantial pain relief and is part of the American College of Rheumatology guidelines for treating osteoarthritis of the knee. Injectable HA has some significant drawbacks, as it is an invasive procedure that involves pain and a chance of introducing an infection in the joint. It also represents a significant cost burden on patients and the health system as it must be administered by a physician and most patients need a series of three to five weekly injections.

Hyaluronic acid is also available in dietary supplement form. Oral HA dietary supplement pills and capsules have been marketed for reducing inflammation, relieve pain, restore joint fluids, protect against cartilage breakdown in osteoarthritis patients as well as for treating chronic fatigue syndrome, chronic pain, fibromyalgia and insomnia. However, HA is difficult to formulate as an effective supplement for oral administration. While most effective in liquid form, HA breaks down over time into lower molecular weight components which are less effective (effectiveness being proportional to the molecular weight) and has a short shelf-life, often less than 9 months from preparation.

In order to maximize stability, and therefore shelf-life, dry solid formulations of HA have been made. However, these formulations have demonstrated low oral bioavailability. During hydration HA swells, becoming viscous and sticky, making it poorly soluble. Consequentially, much of a solid HA formulation does not dissolve or is in a semi-solid state that is eliminated by the body. An alternative is to reconstitute dry solid HA formulations prior to ingestion, however, such formulations typically require more than 24 hours to dissolve with frequent mixing making this approach impractical.

Accordingly, it would be desirable to provide an HA formulation suitable for oral ingestion in which the HA is stable (substantially maintains its high molecular weight) and is readily dissolved having the high bioavailability of a liquid HA formulation.

SUMMARY OF THE INVENTION

In an aspect of the invention there is provided a composition comprising sodium hyaluronate, cyclodextrin, potassium sorbate, and optionally an enzyme wherein said composition is in powder form. In certain embodiments, the composition further comprises sodium benzoate.

In another aspect of the invention there is provided a method for treating a disease, condition or disorder amenable to HA therapy in an animal comprising dissolving a composition of the invention in a solvent to form a solution and administering said solution to an animal.

In an embodiment there is provided a method for reducing inflammation in an animal comprising dissolving a composition of the invention in a solvent to form a solution and administering said solution to an animal.

In another embodiment there is provided a method for relieving pain in an animal comprising dissolving a composition of the invention in a solvent to form a solution and administering said solution to an animal.

In another embodiment there is provided a method for treating chronic fatigue syndrome in an animal comprising dissolving a composition of the invention in a solvent to form a solution and administering said solution to an animal.

In another embodiment there is provided a method treating fibromyalgia in an animal comprising dissolving a composition of the invention in a solvent to form a solution and administering said solution to an animal.

In another embodiment there is provided a method for treating insomnia in an animal comprising dissolving a composition of the invention in a solvent to form a solution and administering said solution to an animal.

In another aspect of the invention there is provided a kit comprising a composition of the invention and a solvent separate from said composition wherein the amount of solvent is capable of dissolving said composition upon mixing.

DETAILED DESCRIPTION OF THE INVENTION

Compositions

The present invention provides solid formulations of hyaluronic acid (HA) that are resistant to degradation into low molecular weight species of HA and yet can be readily dissolved in water. Accordingly, one embodiment of the invention provides a composition comprising sodium hyaluronate, cyclodextrin, optionally sodium benzoate, and potassium sorbate, wherein said composition is in powder form. In another aspect of the invention there is provided a composition comprising sodium hyaluronate, optionally sodium benzoate, and potassium sorbate, wherein said composition is in powder form. In another aspect of the invention there is provided a composition comprising sodium hyaluronate and a preservative, wherein said composition is in powder form. In another aspect of the invention there is provided a composition comprising sodium hyaluronate in an amount less than at least about fifty percent of said composition by weight, wherein said composition is in powder form. In another aspect of the invention there is provided a composition comprising sodium hyaluronate, cyclodextrin, wherein said composition is in powder form.

Compositions of the invention may include additional solid components that do not substantially affect stability of the HA to optimize the properties of the composition for a given use. Additional components may include enzymes, preservatives (e.g., antimicrobial agents), solid carriers (e.g., as finely divided solids such as talc, clay, microcrystalline cellulose, silica, alumina and the like), adjuvants, flavors and fragrances.

In an aspect of the invention there is provided a composition comprising sodium hyaluronate, cyclodextrin, sodium benzoate, potassium sorbate, and an enzyme, wherein said composition is in powder form. In an embodiment, the enzyme is from about 0.001% to about 5% of the composition by weight. In another embodiment, the enzyme is from about 0.01% to about 2% of the composition by weight. In another embodiment, the enzyme is from about 0.05% to about 0.5% of the composition by weight. In another embodiment, the enzyme is about 0.1% of the composition by weight. In another embodiment, the enzyme is 0.1% of the composition by weight.

In a particular embodiment, the sodium hyaluronate has an average molecular weight of at least about 500 kDa. In another embodiment, the sodium hyaluronate has an average molecular weight of about 500 kDa to about 3,500 kDa. In another embodiment, the sodium hyaluronate has an average molecular weight of about 1000 kDa to about 3,000 kDa. In another embodiment, the sodium hyaluronate has an average molecular weight of about 1,000 kDa to about 2,000 kDa. In another embodiment, the sodium hyaluronate has an average molecular weight of about 1,000 kDa to about 1,500 kDa. In yet another embodiment, the sodium hyaluronate has an average molecular weight of no less than 1,000 kDa. In another embodiment, the sodium hyaluronate is "injection grade" i.e. having an average molecular weight of about 2,500 to about 3,500 kDa. In another embodiment, the sodium hyaluronate is "pharmaceutical grade" i.e. having an average molecular weight of about 2,000 to about 3,000 kDa. In another embodiment, the sodium hyaluronate is "food grade" i.e. having an average molecular weight of about 1,000 to about 1,500 kDa. In certain embodiments, the composition is formulated for oral administration. In certain embodiments, at least 25% of the powder dissolves in an aqueous solvent in 15 minutes. In certain embodiments, at least 70% of the powder dissolves in an aqueous solvent in two hours.

In a particular embodiment, the sodium hyaluronate has an average molecular weight of about 10 kDa to about 500 kDa. In another embodiment, the sodium hyaluronate has an average molecular weight of about 100 kDa to about 300 kDa. In another embodiment, the sodium hyaluronate has an average molecular weight of about 200 kDa to about 250 kDa. In certain embodiments, the composition is formulated for topical administration. In certain embodiments, at least 80% of the powder dissolves in an aqueous solvent in 15 minutes. In certain embodiments, at least 95% of the powder dissolves in an aqueous solvent in two hours. In an embodiment, the sodium hyaluronate is less than about 60% of the composition by weight. In an embodiment, the sodium hyaluronate is less than about 50% of the composition by weight. In another embodiment, the sodium hyaluronate is less than about 45% of the composition by weight. In another embodiment, the sodium hyaluronate is less than about 40% of the composition by weight. In an embodiment, the sodium hyaluronate is less than about 35% of the composition by weight. In another embodiment, the sodium hyaluronate is less than about 30% of the composition by weight. In another embodiment, the sodium hyaluronate is less than about 25% of the composition by weight. In another embodiment, the sodium hyaluronate is from about 20% to about 50% of the composition by weight. In another embodiment, the sodium hyaluronate is from about 25% to about 50% of the composition by weight. In another embodiment, the sodium hyaluronate is from about 30% to about 45% of the composition by weight. In another embodiment, the sodium hyaluronate is from about 30% to about 40% of the composition by weight. In another embodiment, the sodium hyaluronate is about 35% of the composition by weight. In another embodiment, the sodium hyaluronate is 35.3% of the composition by weight.

In an embodiment, the cyclodextrin is .alpha. (alpha)-cyclodextrin. In an embodiment, the cyclodextrin is .beta. (beta)-cyclodextrin. In an embodiment, the cyclodextrin is .gamma. (gamma)-cyclodextrin. In an embodiment, the cyclodextrin is modified. In an embodiment, the cyclodextrin is sulfobutyl ether .beta.-cyclodextrin (Captisol®). In an embodiment, the cyclodextrin is 2-hydroxypropyl-.beta.-cyclodextrin.

In an embodiment, cyclrodextrin is from about 0.001% to about 10%, or from about 0.01% to about 5%, or from about 0.1% to about 2.5%, or about 1%, or about 2%, or about 2.5%, or about 3%, or about 4%, of the composition, by weight. In another embodiment, the cyclodextrin is from about 5% to about 75% of the composition by weight. In another embodiment, the cyclodextrin is from about 20% to about 70% of the composition by weight. In another embodiment, the cyclodextrin is from about 30% to about 60% of the composition by weight. In another embodiment, the cyclodextrin is from about 10% to about 30% of the composition by weight. In another embodiment, the cyclodextrin is from about 35% to about 55% of the composition by weight. In another embodiment, the cyclodextrin is about 40% to about 45% of the composition by weight. In another embodiment, the cyclodextrin is 42.8% of the composition by weight.

In another embodiment, the sodium benzoate is from about 0.1% to about 10% of the composition by weight. In another embodiment, the sodium benzoate is from about 0.5% to about 5% of the composition by weight. In another embodiment, the sodium benzoate is 0% of the composition by weight. In another embodiment, the sodium benzoate is from about 1% to about 3% of the composition by weight. In another embodiment, the sodium benzoate is about 3% of the composition by weight. In another embodiment, the sodium benzoate is 2.7% of the composition by weight.

In another embodiment, the potassium sorbate is from about 0.1% to about 10% of the composition by weight. In another embodiment, the potassium sorbate is from about 0.5% to about 5% of the composition by weight. In another embodiment, the potassium sorbate is from about 2% to about 4% of the composition by weight. In another embodiment, the potassium sorbate is 0% of the composition by weight. In another embodiment, the potassium sorbate is about 3% of the composition by weight. In another embodiment, the potassium sorbate is 3.2% of the composition by weight.

In another embodiment, the compositions of the invention further comprise sodium chloride. In an embodiment, the sodium chloride is from about 0.1% to about 15% of the composition by weight. In an embodiment, the sodium chloride is 0% of the composition by weight. In another embodiment, the sodium chloride is from about 1% to about 10% of the composition by weight. In another embodiment, the sodium chloride is from about 3% to about 8% of the composition by weight. In another embodiment, the sodium chloride is about 5% of the composition by weight. In another embodiment, the sodium chloride is 5.3% of the composition by weight.

In another embodiment, the compositions of the invention further comprise citric acid. In an embodiment, the citric acid is from about 0.5% to about 25% of the composition by weight. In another embodiment, the citric acid is from about 1% to about 20% of the composition by weight. In an embodiment, the citric acid is 0% of the composition by weight. In another embodiment, the citric acid is from about 5% to about 15% of the composition by weight. In another embodiment, the citric acid is about 10% of the composition by weight. In another embodiment, the citric acid is 10.7% of the composition by weight.

In another embodiment, the compositions of the invention further comprise bamboo gum. In an embodiment, the bamboo gum is from about 0.5% to about 25% of the composition by weight. In another embodiment, the bamboo gum is from about 1% to about 20% of the composition by weight. In another embodiment, the bamboo gum is 0% of the composition by weight. In another embodiment, the bamboo gum is from about 5% to about 15% of the composition by weight. In another embodiment, the bamboo gum is about 10% of the composition by weight. In another embodiment, the bamboo gum is 10.7% of the composition by weight.

In another embodiment, the compositions of the invention further comprise Himalayan pink salt. In an embodiment, the enzyme is from about 0.001% to about 5% of the composition by weight. In another embodiment, the Himalayan pink salt is from about 0.01% to about 2% of the composition by weight. In another embodiment, the Himalayan pink salt is from about 0.05% to about 0.5% of the composition by weight. In an embodiment, the Himalayan pink salt is 0% of the composition by weight. In another embodiment, the Himalayan pink salt is about 0.1% of the composition by weight. In another embodiment, the Himalayan pink salt is 0.1% of the composition by weight.

In an embodiment, a formulation according to the invention comprises xanthan gum. In an embodiment, xanthan gum is from about 0.001% to about 50%, or from about 0.01% to about 40%, or from about 0.1% to about 30%, or from about 1% to about 20%, or about 10% or about 20%, or about 30%, or about 40%, of the composition, by weight. In another embodiment, the compositions of the invention lack xanthan gum.

In another embodiment, the compositions of the invention further comprise an enzyme or enzyme blend, for example, a blend of digestive enzymes. In an embodiment, the enzyme or enzyme blend is from about 0.001% to about 5% of the composition by weight. In another embodiment, the enzyme or enzyme blend is from about 0.01% to about 2% of the composition by weight. In another embodiment, the enzyme or enzyme blend is from about 0.05% to about 0.5% of the composition by weight. In an embodiment, the enzyme or enzyme blend is 0% of the composition by weight. In another embodiment, the enzyme or enzyme blend is about 0.1% of the composition by weight. In another embodiment, the enzyme or enzyme blend is 0.1% of the composition by weight.

Compositions of the invention may be prepared according to routine formulation techniques from commercially available ingredients.

In another aspect of the invention there is provided an oral treatment composition comprising contacting the composition of the invention with an aqueous solvent. In certain embodiments, wherein after storage at room temperature for three months the sodium hyaluronate has an average molecular weight of about 800 kDa to about 3,000 kDa. In certain embodiments, less than 10% of the sodium hyaluronate has an actual molecular weight of less than about 150 kDa. In certain embodiments, after storage at room temperature for six months less than 50% the sodium hyaluronate has an actual molecular weight of less than about 500 kDa. In certain embodiments, the sodium hyaluronate has an average molecular weight of about 1,000 kDa to about 3,000 kDa when administered to the animal. In certain embodiments, the sodium hyaluronate has an average molecular weight of about 2000 kDa when administered to the animal. In certain embodiments, less than 10% of the sodium hyaluronate has an actual molecular weight of less than about 200 kDa when administered to the animal. It is desirable to avoid the presence of low molecular weight sodium hyaluronate in an oral formulation because low molecular weight sodium hyaluronate can have detrimental physiological properties, such as being carcinogenic, pro-inflammatory, and/or increasing cancer angiogenesis. In certain embodiments, at least 20% of the powder dissolves in an aqueous solvent in 15 minutes. In certain embodiments, at least 70% of the powder dissolves in an aqueous solvent in two hours. In a certain embodiment, the powder comprises the following molecular weight distribution:

1) 68% is between about 600 kDa and about 1800 kDa,
2) 95% is between about 350 kDa and about 2000 kDa, and
3) the average is about 1200 kDa.

In another aspect of the invention there is provided a topical treatment composition comprising contacting the composition of the invention with an aqueous solvent.

In another aspect of the invention there is provided a topical treatment composition made by a method of the invention. In certain embodiments, after storage at room temperature for three months the sodium hyaluronate has an average molecular weight of about 10 kDa to about 500 kDa. In certain embodiments, less than 10% of the sodium hyaluronate has an actual molecular weight of less than about 10 kDa. In certain embodiments, after storage at room temperature for six months less than 50% the sodium hyaluronate has an actual molecular weight of less than about 10 kDa. In another aspect of the invention there is provided a method, wherein the sodium hyaluronate has an average molecular weight of about 10 kDa to about 500 kDa when administered to the animal. In certain embodiments, less than 5% of the sodium hyaluronate has an actual molecular weight of less than about 50 kDa when administered to the animal. In certain embodiments, less than 10% of the sodium hyaluronate has an actual molecular weight of less than about 50 kDa when administered to the animal. In certain embodiments, at least 50% of the powder dissolves in an aqueous solvent in 15 minutes. In certain embodiments, at least 90% of the powder dissolves in an aqueous solvent in two hours.

Indications

In an aspect of the invention there is provided a method for treating a disease, condition or disorder amenable to HA therapy in an animal comprising dissolving a composition of the invention in a solvent to form a solution and administering said solution to an animal. In an embodiment, the solvent is a pharmaceutically acceptable carrier or diluent. In another embodiment, the solvent is water. In an embodiment, the water is sterile. In an embodiment, the composition is dissolved in a fruit juice e.g. orange juice. In an embodiment, the amount of HA in the solution is about 1 mg to 500 mg per teaspoon. In an embodiment, the amount of HA in the solution is about 5 mg to 250 mg per teaspoon. In an embodiment, the amount of HA in the solution is about 10 mg to 200 mg per teaspoon. In an embodiment, the amount of HA in the solution is about 20 mg to 150 mg per teaspoon. In an embodiment, the amount of HA in the solution is about 30 mg to 100 mg per teaspoon. In an embodiment, the amount of HA in the solution is about 60 mg per teaspoon. In an embodiment, the amount of HA in the solution is 60 mg per teaspoon. In certain embodiments, the resulting solution comprises 0.5 to 5% sodium hyaluronate. In certain embodiments, the resulting solution comprises 1 to 2% sodium hyaluronate.

In an embodiment the solution is administered orally to the animal. In an embodiment, the solution is mixed immediately upon adding the composition to the solvent. In an embodiment the solution is mixed (e.g., shaken or stirred) for at least 10 seconds. In another embodiment, the composition is mixed in the solvent for at least 20 seconds. In another embodiment, the composition is mixed in the solvent for less than 30 seconds. In another embodiment, the composition is mixed in the solvent for at least 30 seconds. In another embodiment, the composition is mixed in the solvent for at least 1 minute. In another embodiment, the composition is mixed in the solvent for at least 5 minutes. In another embodiment, the solution is remixed about every 5 minutes. In another embodiment, the solution is remixed about every 15 minutes. In an embodiment, the solution is remixed for at least 10 minutes. In an embodiment, the solution is remixed for at least 15 minutes. In an embodiment, the solution is remixed for at least 30 minutes. In an embodiment, the solution is mixed and remixed for at least 60 minutes. In an embodiment, the solution is mixed and remixed for at least 90 minutes.

In an embodiment, the solution is mixed, allowed to sit for a period of time, and then remixed. In certain embodiments, the solution is mixed for 1 to 30 seconds (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 seconds). In certain embodiments, the solution is allowed to sit for a period of time (i.e., allowed to hydrate), which time is between 5 minutes and 60 minutes. In certain embodiments, the solution hydrates overnight (e.g., 8, 9, 10, 11, 12, 13, 14, 15, 16, 17, 18, 19, 20, 21, 22, 23, or 24 hours). In certain embodiments, the solution is remixed for 1 to 30 seconds (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 seconds). In certain embodiments, the hydration and remixing can occur multiple times. In an embodiment, the solution is remixed immediately prior to administration.

The amount of solution administered to the animal will depend on the particular species of animal as well as age, gender and ethnicity, the particular indication being treated and the particular ingredients and amounts of the composition. A physician or veterinarian may provide the amount of solution to be administered. For example, a human being treated for osteoarthritis or for improving joint function may be administered about 5 mg to about 500 mg per day. In a particular embodiment the amount administered is about 10 mg to about 150 mg per day. In a particular embodiment the amount administered is about 20 mg to about 100 mg per day. In a particular embodiment the amount administered is about 50 mg to about 80 mg per day. In a particular embodiment the amount administered is about 60 mg per day. In a particular embodiment the amount administered is 60 mg per day. Useful dosages of the solution can also be determined by comparing the in vitro activity, and in vivo activity of the solution in animal models. Methods for the extrapolation of effective dosages in mice, and other animals, to humans are known to the art; for example, see U.S. Pat. No. 4,938,949.

In an embodiment, the animal is a vertebrate. In an embodiment, the animal is a mammal. In an embodiment, the animal is a human. In an embodiment, the animal is feline. In an embodiment, the animal is canine. In an embodiment, the animal is equine. In an embodiment, the animal is bovine. In an embodiment, the animal is porcine. In an embodiment, the animal is ovine.

In another embodiment there is provided a method for improving joint or ligament function in an animal comprising dissolving a composition of the invention in a solvent to form a solution and administering said solution to an animal. In another embodiment there is provided a method for improving joint or ligament function in an animal comprising dissolving a composition of the invention in a solvent to form a solution and administering said solution to an animal. In an embodiment there is provided a method for reducing inflammation (e.g., joint inflammation) in an animal comprising dissolving a composition of the invention in a solvent to form a solution and administering said solution to an animal. In another embodiment there is provided a method for treating a wound (i.e., wound repair) in an animal comprising dissolving a composition of the invention in a solvent to form a solution and administering said solution to an animal.

In another embodiment there is provided a method for relieving pain in an animal comprising dissolving a composition of the invention in a solvent to form a solution and administering said solution to an animal. In another embodiment there is provided a method for treating chronic fatigue syndrome in an animal comprising dissolving a composition of the invention in a solvent to form a solution and administering said solution to an animal. In another embodiment there is provided a method treating fibromyalgia in an animal comprising dissolving a composition of the invention in a solvent to form a solution and administering said solution to an animal. In another embodiment there is provided a method for treating insomnia in an animal comprising dissolving a composition of the invention in a solvent to form a solution and administering said solution to an animal. In another aspect of the invention there is provided a method of making an oral treatment composition comprising contacting the composition of the invention with an aqueous solvent.

The present invention is superior to currently available formulations, because it enables HA to be readily dissolved by a consumer. Current marketed HA products in powder form (and including the usual components) will not easily dissolve in water, nor are the current marketed powders/solid forms intended processing by the consumer. HA has to be in liquid form when consumed to be easily absorbed. The present formula allows the consumer to easily perform the operations that are normally done by the manufacturer (with much effort) to produce the liquid products on the market. The primary reason for our product is that the consumer can make it fresh, just before usage.

Powdered HA gets extremely thick and gels when mixed with water. The viscosity (thickness) of HA in solution is related to its MW, the greater the MW the greater the viscosity (thickness or gelling) and the more difficult to get into solution. The speed of dissolving is related to the MW of the HA. Low MW HA solutions are not as thick and the Low MW HA is not difficult to dissolve; however, high MW HA clumps to a much higher degree. High MW HA clumps take many hours to dissolve and only if almost constantly agitated, because in that form it cannot hydrate evenly.

Kits

In another aspect of the invention there is provided a kit comprising a composition of the invention and instructions for dissolving said composition in a solvent and administering the resulting solution to an animal. In another aspect of the invention there is provided a kit comprising a composition of the invention and a solvent separate from said composition wherein the amount of solvent is capable of dissolving said composition upon mixing. In an embodiment, the solvent is in a glass vial. In an embodiment, the solvent is in a plastic vial.

Additional Embodiments and/or Examples

The invention provides inter alia a delivery system for a consumer, for example, a hyaluronic acid (hyaluronan, HA) delivery system for a consumer, and, more specifically, a dry formula that a consumer can make into a solution, a solid powder HA formulation that is very stable and suitable for long-term storage. A consumer, even relatively shortly before the time of administration, may readily make an aqueous solution out of such a solid powder HA formulation; this is in contrast to the difficulty or impossibility of readily and rapidly making an aqueous solution from HA alone plus water. An aqueous solution such as a consumer can make by mixing an HA powder formulation with water provides a liquid form of HA that is a more bioavailable dosage form compared to solid dosage forms (powders, capsules, tablet, etc.). HA is unstable when in liquid form, quickly degrading into smaller molecular weight fragments which are inflammatory and detrimental to health. High molecular weight HA is stable in solid form and is anti-inflammatory and beneficial to health. A dry formulation such as is provided by the invention may have shelf-life of at least 3 years. A liquid formulation, such as may be prepared by the consumer by mixing a dry formulation according to the invention with water, has a shelf-life of at least 2-3 months. Various weight amounts of dry formula can be packaged for final volumes and concentrations of the active ingredients allowing the same formulation to be used for many types of oral products suitable for consumption by all animals and dosage needs. A formulation according to the invention may be provided to the consumer in a suitable container-closure system known in the pharmaceutical arts. For example, a method for preparation by a consumer of an aqueous HA solution from a dry HA formulation and water may comprise the following steps as typically may be set forth in instructions for the consumer:
   a. fill container partially (about 10% of volume) with water and mix;
   b. wait 10 min and fill container to volume with water;
   c. mix and sit bottle on its side;
   d. wait about 1 hour and repeat c.;
   e. wait about 1 hour and repeat c.;
   f. repeat c. if necessary If time is not critical, one may perform operations a. through c. and let sit overnight. In still another example, a consumer may add into a container containing a formulation according to the invention an amount of water sufficient to fill the container and then agitate or shake the contents of the container, and optionally agitate or shake the contents of the container one or more further times, such that, after an interval of approximately one hour, or approximately two hours, or approximately three hours, after the adding of the amount of water sufficient to fill the container, the formulation is dissolved in the water. In another further example, a formulation according to the invention is contained in a first container having a form of a packet or a sachet, similar to a container known in the food science and/or consumer products arts in the United States for containing a serving of a condiment, such as ketchup, or syrup, or sugar, or salt, or pepper, or tea. In such a further example, a volume of water is contained in a second container, or is placed into a second container subsequent to a dispensing of an amount of a formulation according to the invention into the second container. An amount of a formulation according to the invention is dispensed from the first container into the second container, and the amount of formulation so dispensed is contacted with and admixed with the amount of water that is contained in or that has been placed into the second container to make a mixture, and the mixture is optionally agitated or shaken such that, after an interval of approximately one hour, or approximately two hours, or approximately three hours, the mixture in the second container is in the form of a viscous solution.

In the following table, to be considered part of this paragraph, are various (16) examples of a formulation according to the invention; each row in a numbered column in the table states the weight % of the respective ingredient in dry form:

| INGREDIENT | 1 | 2 | 3 | 4 | 5 | 6 | 7 | 8 |
| --- | --- | --- | --- | --- | --- | --- | --- | --- |
| Hyaluronic Acid | 30 | 2 | 15 | 20 | 10 | 15 | 5 | 40 |
| alpha-Cyclodextrin | 2.5 |  | 5 | 10 | 2 | 10 | 5 | 10 |
| Citric Acid | 10 |  | 10 | 5 |  | 5 | 5 | 10 |
| Potassium Sorbate | 2.5 | 2 | 2 | 2 | 2 | 3 | 2 | 2 |
| Sodium Benzoate | 2.5 | 2 | 2 | 2 | 2 | 3 | 2 | 2 |
| Sodium Chloride | 2.5 |  | 2 | 2 | 4 | 4 | 1 | 1 |
| D-Mannitol | 50 |  | 10 | 20 |  | 20 | 5 | 35 |
| Ascorbic Acid |  |  | 3 |  |  |  |  |  |
| Sorbitol |  |  |  | 39 |  |  | 5 |  |
| EDTA, Disodium |  |  | 1 |  |  |  |  |  |
| Chondroitin Sulfate, Na |  | 26 | 15 |  | 15 | 10 | 20 |  |
| D-Glucosamine HCl |  | 37 | 20 |  | 15 | 10 | 25 |  |
| Methyl Sulfonylmethane |  | 26 | 15 |  | 15 | 10 | 10 |  |
| Manganese Sulfate |  | 1.3 |  |  |  |  | 1 |  |
| Calcium Ascorbate |  | 3.7 |  |  |  | 5 | 4 |  |
| Polyphenols* |  |  |  |  |  | 5 | 5 |  |
| Type II Collagen |  |  |  |  | 20 |  |  |  |

| INGREDIENT | 9 | 10 | 11 | 12 | 13 | 14 | 15 | 16 |
|---|---|---|---|---|---|---|---|---|
| Flavoring | | | | | 5 | | | |
| alpha-Lipoic Acid | | | | | 10 | | 5 | |
| Hyaluronic Acid | 50 | 35 | 35 | 30 | 10 | 5 | 5 | 38 |
| alpha-Cyclodextrin | 15 | 5 | 5 | 2.5 | 3 | 2 | 2 | 45 |
| Citric Acid | 10 | 10 | 10 | 10 | 2 | 2 | 2 | 8 |
| Potassium Sorbate | 2 | 2 | 2 | 2.5 | 2 | 2 | 2 | 6 |
| Sodium Benzoate | 2 | 2 | 2 | 2.5 | 2 | 2 | 2 | |
| Sodium Chloride | 1 | 6 | 6 | 2.5 | 1 | 2 | 2 | 3 |
| D-Mannitol | 20 | 40 | 20 | 40 | 5 | 5 | 5 | |
| Ascorbic Acid | | | | | 3 | | | |
| Sorbitol | | | 20 | | 8 | 5 | 5 | |
| EDTA, Disodium | | | | | 1 | 1 | 1 | |
| Chondroitin Sulfate, Na | | | | | 10 | 10 | 10 | |
| D-Glucosamine HCl | | | | | 25 | 30 | 30 | |
| Methyl Sulfonylmethane | | | | | 5 | 10 | 10 | |
| Manganese Sulfate | | | | | 1 | 1 | 1 | |
| Calcium Ascorbate | | | | | 5 | | 4 | |
| Polyphenols* | | | | 5 | 5 | 4 | 4 | |
| Type II Collagen | | | | | 5 | 10 | 10 | |
| Flavoring | | | | | 5 | 5 | 5 | |
| alpha-Lipoic Acid | | | | 5 | 5 | 1 | | |

*Pycnogenol, Pine Bark Extract, Curcumin, flavonoids

To make such a formulation, dry ingredients are weighed and mixed thoroughly, for example, by hand with a mixing utensil, or using automated means such as a commercial dry-ingredient mixer such as is known in the pharmaceutical and/or dietary supplement and/or food-preparation arts, in a suitable container such as a large bowl. Such a formulation is used as described above, by mixing the formulation with water and then administering the resultant aqueous mixture to a mammalian subject in need of a benefit conferred by such a mixture. A benefit conferred by such a mixture includes, for example, support of joint health, support of immune health, support of cardiovascular health.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the term "about" refers to a value +/−5% of the given value.

Embodiments of this invention are described herein, including the best mode known to the inventor for carrying out the invention. Variations of those embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A solid dry powder formulation consisting of hyaluronic acid and potassium sorbate and alpha-cyclodextrin and citric acid and sodium benzoate and sodium chloride and D-mannitol and optionally sorbitol, wherein the solid powder formulation is susceptible of dissolution in an amount of water sufficient to fill a container containing the solid powder formulation after an interval of one hour following filling the container containing the solid powder formulation with the amount of water sufficient to fill the container containing the solid powder formulation, and wherein the formulation consists of, by weight, 30% or 35% hyaluronic acid and 2.5% or 5% alpha-cyclodextrin.

2. The solid dry powder formulation of claim 1, the formulation consisting of, by weight: 30% hyaluronic acid; 2.5% alpha-cyclodextrin; 10% citric acid; 2.5% potassium sorbate; 2.5% sodium benzoate; 2.5% sodium chloride; and 50% D-mannitol.

3. The solid dry powder formulation of claim 1, the formulation consisting of, by weight: 35% hyaluronic acid; 5% alpha-cyclodextrin; 10% citric acid; 2% potassium sorbate; 2% sodium benzoate; 6% sodium chloride; 20% D-mannitol; and 20% sorbitol.

* * * * *